(12) United States Patent
Ko

(10) Patent No.: US 11,439,459 B2
(45) Date of Patent: Sep. 13, 2022

(54) TREATMENT DEVICE AND TREATMENT METHOD USING SAME

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 603 days.

(21) Appl. No.: 16/066,654

(22) PCT Filed: Aug. 12, 2016

(86) PCT No.: PCT/KR2016/008870
§ 371 (c)(1),
(2) Date: Jun. 27, 2018

(87) PCT Pub. No.: WO2018/030561
PCT Pub. Date: Feb. 15, 2018

(65) Prior Publication Data
US 2019/0000541 A1    Jan. 3, 2019

(51) Int. Cl.
*A61B 18/14* (2006.01)
*A61N 1/06* (2006.01)
(Continued)

(52) U.S. Cl.
CPC ........... *A61B 18/1477* (2013.01); *A61M 5/46* (2013.01); *A61M 37/0015* (2013.01); *A61N 1/06* (2013.01);
(Continued)

(58) Field of Classification Search
CPC ...... A61B 18/1477; A61B 2018/00011; A61B 2018/00023; A61B 2018/1475;
(Continued)

(56) References Cited

U.S. PATENT DOCUMENTS

2007/0060989 A1*  3/2007  Deem ................ A61B 18/1477
                                                              607/99
2008/0009811 A1    1/2008  Cantor
(Continued)

FOREIGN PATENT DOCUMENTS

| KR | 1020130012805 A | 2/2013 |
| KR | 1020130137409 A | 12/2013 |
| KR | 101703290 B1 | 2/2017 |

OTHER PUBLICATIONS

International Search Report for PCT/KR2016/008870 dated May 11, 2017.

*Primary Examiner* — Thomas A Giuliani

(57) ABSTRACT

A high-frequency treatment device according to the present invention can comprise: a handpiece; a plurality of needles formed on one side of the handpiece so as to be able to come out and retract, and receiving a high-frequency current; and a pressing part disposed in the coming out and retracting direction of the plurality of needles, and tensing the skin by applying a predetermined pressure to the skin. The high-frequency treatment device according to the present invention has an effect of enabling pain occurring due to the insertion of a plurality of conventional needles to be alleviated by adjusting the tension of a patient's skin before inserting a plurality of needles such that the needles are smoothly inserted into the skin.

10 Claims, 12 Drawing Sheets

(51) Int. Cl.
  *A61N 1/32* (2006.01)
  *A61N 1/40* (2006.01)
  *A61M 5/46* (2006.01)
  *A61N 1/08* (2006.01)
  *A61M 37/00* (2006.01)
  *A61B 90/00* (2016.01)
  *A61B 18/00* (2006.01)

(52) U.S. Cl.
  CPC ............... *A61N 1/08* (2013.01); *A61N 1/328* (2013.01); *A61N 1/40* (2013.01); *A61B 2018/0047* (2013.01); *A61B 2018/143* (2013.01); *A61B 2018/1467* (2013.01); *A61B 2018/1475* (2013.01); *A61B 2090/062* (2016.02); *A61B 2090/065* (2016.02); *A61M 2205/3344* (2013.01); *A61M 2205/50* (2013.01); *A61M 2205/505* (2013.01)

(58) Field of Classification Search
  CPC .... A61B 2018/1425; A61B 2018/1427; A61B 2018/143; A61B 2018/1467; A61B 2018/00452; A61B 2018/0047; A61B 2018/00005; A61N 1/328; A61N 1/40; A61N 1/06; A61N 1/08; A61M 5/46; A61M 37/0015; A61M 2205/3344
  USPC .......... 606/41, 42, 44, 45, 49; 607/3, 98, 99, 607/101, 113, 115, 116
  See application file for complete search history.

(56) References Cited

U.S. PATENT DOCUMENTS

| | | | |
|---|---|---|---|
| 2008/0091183 A1* | 4/2008 | Knopp | A61N 1/328 606/31 |
| 2008/0215039 A1* | 9/2008 | Slatkine | A61M 5/425 606/9 |
| 2014/0194789 A1* | 7/2014 | Ko | A61B 5/6848 601/18 |

* cited by examiner

TREATMENT DEVICE AND TREATMENT METHOD USING SAME

CROSS-REFERENCE TO RELATED APPLICATION

This application is a National Phase of International Application No. PCT/KR2016/008870, filed Aug. 12, 2016, which is hereby incorporated by reference in its entirety.

TECHNICAL FIELD

The present invention relates to a treatment apparatus and a treatment method using the same and, more particularly, to a treatment apparatus transferring RF energy through needles inserted into a tissue and a treatment method using the same.

BACKGROUND ART

When RF energy is transferred to the inside of the human body, deep heat is generated in a tissue of the human body. The deep heat is bioheat generated by a rotary motion, distortion, a collision motion, etc. attributable to the frication of molecules forming the tissue of the human body while the molecules are vibrated by RF energy.

A treatment apparatus for transferring RF energy using micro needles as electrodes has recently been developed and used as a method for treating the skin, such as acne treatment, a pore reduction, wrinkle removal, and scar removal. Korean Patent Application Publication No. 10-2013-0012805 discloses such an apparatus.

The micro needle of the treatment apparatus can reach up to the dermal layer through the outer layer of the skin. Accordingly, the treatment apparatus using the micro needle has an advantage in that it improves treatment efficiency by transferring RF energy up to the dermal layer.

The treatment apparatus uses a method of inserting a plurality of micro needles into the skin at the same time. If the plurality of micro needles is inserted into the skin at the same time, there is a problem in that the micro needles may not be smoothly inserted depending on surface resistance of the skin although the diameter of the micro needle is very small.

Furthermore, when lots of the micro needles are inserted into the skin at the same time, there is a problem in that a patient who undergoes treatment feels pain because the pain is doubled.

DISCLOSURE

Technical Problem

An object of the present invention is to provide a treatment apparatus capable of improving a user's surgical procedure convenience and reducing paid felt by a patient when a plurality of needles is inserted by making skin tension reach up to a specific value so that the plurality of needles is smoothly inserted into the skin, and a treatment method using the same.

Technical Solution

A treatment apparatus according to the present invention may include a handpiece; a plurality of needles formed to advance and retract on one side of the handpiece and supplied with a high frequency current; and a pressurization unit positioned in the direction in which the plurality of needles advances and retracts and providing tension to a skin by applying given pressure to the skin.

Furthermore, the RF energy treatment apparatus may further include a sensing unit sensing a force of the pressurization unit applied to the skin so that the tension of a given amount or more is generated in the skin before the plurality of needles is inserted into the skin.

Furthermore, the RF energy treatment apparatus may further include an indicating unit indicating the tension of the skin so that a user can recognize the tension of the skin when the tension of the skin according to the pressurization of the pressurization unit reaches a given value or more in the sensing unit.

Furthermore, when the tension of the skin according to the pressurization of the pressurization unit has the given value or more, the sensing unit may transmit a signal to a controller so that the plurality of needles is inserted into the skin simultaneously or sequentially.

Furthermore, the pressurization unit may be position on a surface of the end of the handpiece and on one side where the plurality of needles advances and retracts or may be positioned at the edge of a surface outside through holes through which the plurality of needles penetrates. The surface of the edge may form a step along with the surface in which the through holes is formed.

Furthermore, the sensing unit may include at least one pressure sensor positioned on a surface of the edge forming the pressurization unit.

Furthermore, the force applied by the pressurization unit may be 1N or more so that the tension of the given amount or more is generated in the skin.

Furthermore, the RF energy treatment apparatus may further include a current connector positioned within the handpiece to supply current to the sensing unit and supply the high frequency current to the plurality of needles.

Furthermore, the RF energy treatment apparatus may further include a support plate supporting the plurality of needles and a displacement measurement sensor positioned at a location neighboring the support plate to measure a depth of the needles inserted into the skin.

Furthermore, the displacement measurement sensor is positioned on the outside of the plurality of needles, and may measure the moving displacement interval of the plurality of needles that moves in a length direction by the driving of the support plate.

An RF energy treatment apparatus according to the present invention may include an RF generator generating a high frequency current; a connection unit drawn out from the RF generator to supply the high frequency current; a handpiece connected to the connection unit; a plurality of needles electrically connected by the connection unit and supplied with the high frequency current; and a pressurization unit positioned in the direction in which the plurality of needles advances and retracts and providing tension of the skin by applying given pressure to the skin.

An RF energy treatment method according to the present invention may include the steps of applying, by the pressurization unit of a handpiece, given pressure to the skin; generating tension of a given amount or more in the skin through the applied pressure; and transmitting a signal to a controller so that a plurality of needles is inserted into the skin at the same time or sequentially when the tension of the skin has a given value or more.

Furthermore, the RF energy treatment method may further include the step of sensing, by a sensing unit, a force of the pressurization unit applied to the skin after the step of generating the tension of the given amount in the skin through the applied pressure.

Furthermore, the RF energy treatment method may further include the step of receiving a signal from the sensing unit and indicating the tension of the skin so that a user can recognize the tension of the skin when the tension of the skin reaches the given value or more after the step of sensing, by the sensing unit, the force of the pressurization unit applied to the skin.

Furthermore, the RF energy treatment method may further include the step of adjusting the moving displacement of the plurality of needles when the plurality of needles is inserted into the skin at the same time or sequentially.

Detailed contents of other embodiments are included in the detailed description and the drawings.

Advantageous Effects

The treatment apparatus according to the present invention has advantages in that it can improve an operator's use convenience and reduce pain felt by a patient when the micro needles are inserted because the apparatus is configured to insert the needles in the state in which tension has been provided to make the skin taut.

MODE FOR INVENTION

Hereinafter, a treatment apparatus and a treatment method using the same according to embodiments of the present invention are described in detail with reference to the accompanying drawings. However, terms or words disclosed in the followings of the present embodiment should not be construed as having common or dictionary meanings, but should be construed as having meanings and concepts that comply with the technological spirit of the present invention based on the principle that an inventor may appropriately define the concept of a term in order to describe his or her invention in the best manner.

Accordingly, elements shown in the embodiments and drawings described in this specification are only the most preferred embodiments of the present invention and do not fully represent the technological spirit of the present invention. Accordingly, it would be understood that a variety of equivalents and modifications which may substitute the embodiments at the time of filing of this application may be present.

Figure 1:
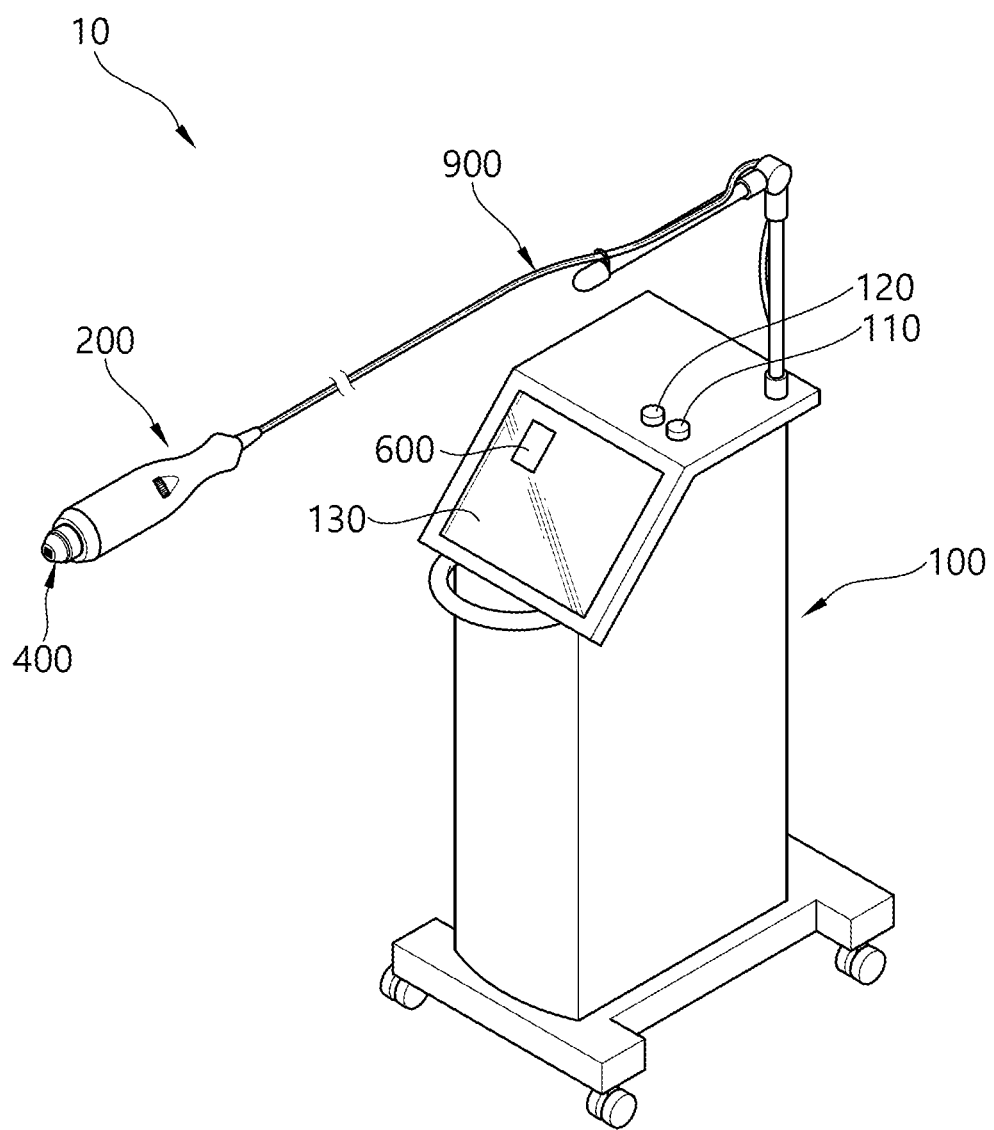
FIG. 1 is a perspective view showing an RF treatment apparatus according to an embodiment of the present invention.
Figure 2:
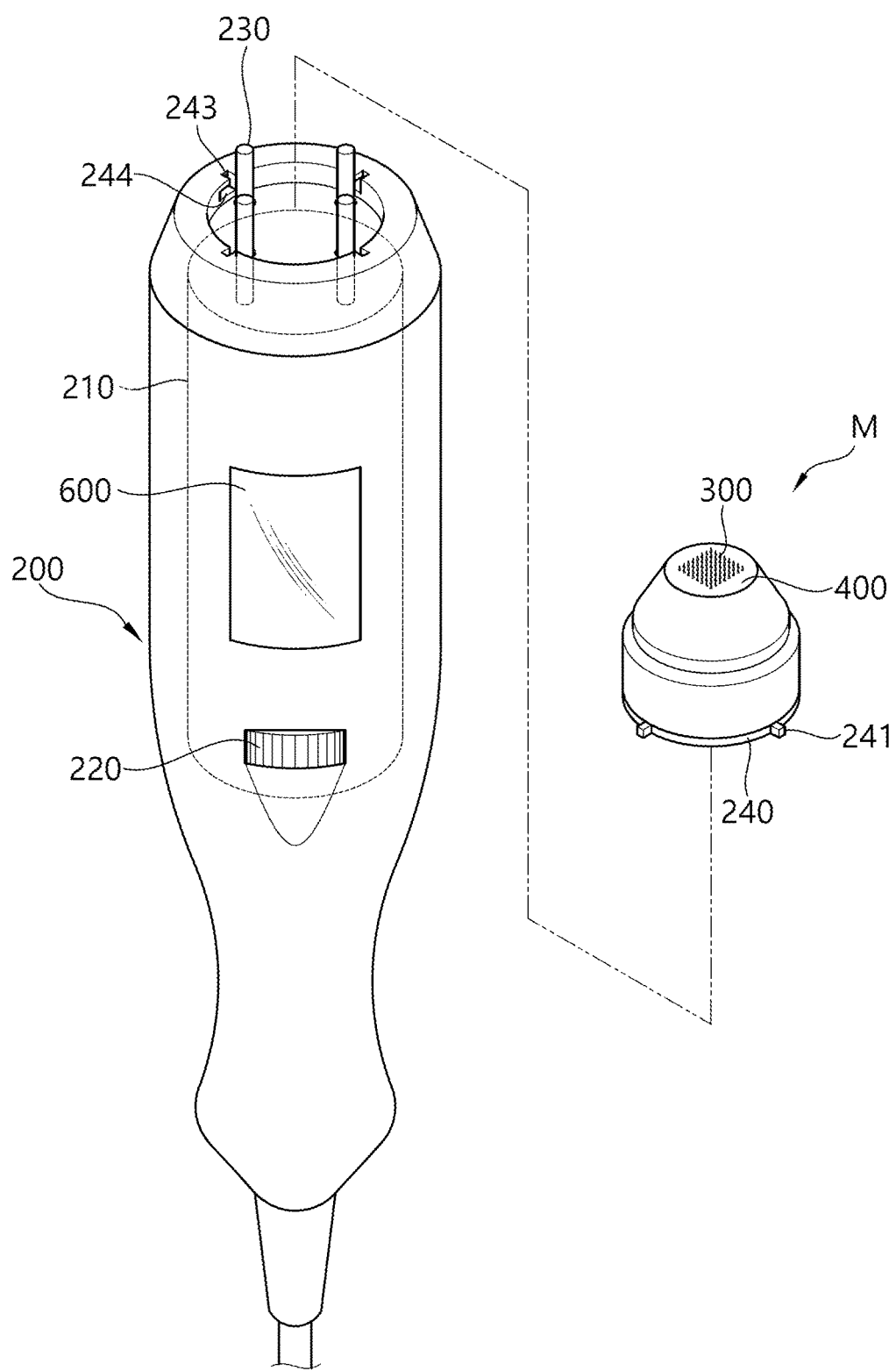
FIG. 2 is a perspective view showing the handpiece of the RF treatment apparatus according to an embodiment of the present invention.

FIG. 1 is a perspective view showing an RF treatment apparatus according to an embodiment of the present invention. FIG. 2 is a perspective view showing the handpiece of the RF treatment apparatus according to an embodiment of the present invention.

Referring to FIGS. 1 and 2, the treatment apparatus 10 according to the present invention includes a main body 100 equipped with an RF generator, a handpiece 200, a plurality of needles 300, a pressurization unit 400, and a connection unit 900.

The RF generator may be provided in the main body 100. The RF generator generates RF energy used for treatment. The frequency of the RF energy generated by the RF generator may be controlled depending on the physical constitution, treatment purpose, a treatment portion, etc. of a patient. For example, RF energy used for skin treatment may be controlled in the range of 0.1 to 0.8 MHz.

Furthermore, a power on/off switch 110, a frequency control lever 120 capable of controlling the frequency of RF energy generated by the RF generator, and a touch screen 130 displaying a variety of types of information including the operation contents of the treatment apparatus and enabling a user to enter a command may be positioned in the main body.

Meanwhile, the handpiece 200 is connected to the main body 100 by the connection unit 900. The connection unit 900 may transfer RF energy generated by the RF generator of the main body to the plurality of needles 300, and may transfer power from the main body, which is necessary to drive various devices of the handpiece 200. The connection unit 900 is configured in a cable form, and a cable including a plurality of conducting wires whose metal lines have been surrounded with insulating coating may be used as the connection unit.

A needle adjustment member 210 is positioned in the handpiece 200. The needle adjustment member 210 is an element capable of linearly moving output terminals 230 in the length direction. As the output terminals linearly move, the plurality of needles disposed at the end of the output terminals may advance and retract to and from the outside of the pressurization unit. Accordingly, when the needle adjustment member 210 is driven, the plurality of needles may be inserted into a tissue of a patient or drawn out from a tissue of a patient during treatment. A solenoid or a linear actuator, such as a hydraulic/pneumatic cylinder, may be used as the needle adjustment member 210.

Furthermore, a displacement adjustment member 220 may be positioned in the outer wall of the handpiece 200. The displacement adjustment member 220 is an element for controlling the linear moving distance of the output terminal 230, and may be configured in such a way as to change the movable range of the needle adjustment member by control of the displacement adjustment member. A user may control the depth of the plurality of needles 300 inserted into the skin by manipulating the displacement adjustment member 200.

A tip module M is provided at the end of the handpiece. The tip module M includes the plurality of needles 300 and may be detachably positioned in the handpiece. Specifically, a base 240 forms the bottom of the tip module M. Detachment protrusions 241 that have been outward protruded are formed on the outer wall of the base 240. Furthermore, guide grooves 243 guiding the detachment protrusions 241, and an anti-separation groove 244 communicating with the guide grooves 243 and preventing the detachment protrusions 241 guided along the guide grooves 243 from breaking away in the length direction of the handpiece 200 are formed in a recess unit to which the tip module is coupled in the handpiece 200. Accordingly, the tip module is positioned in the handpiece 200 in such a manner that the detachment protrusions 241 are coupled to the anti-separation groove 244. In this case, as in the present embodiment, an embodiment in which the tip module M is detachably positioned in the handpiece is an example, and the tip module may be integrated with the handpiece.

Figure 3:
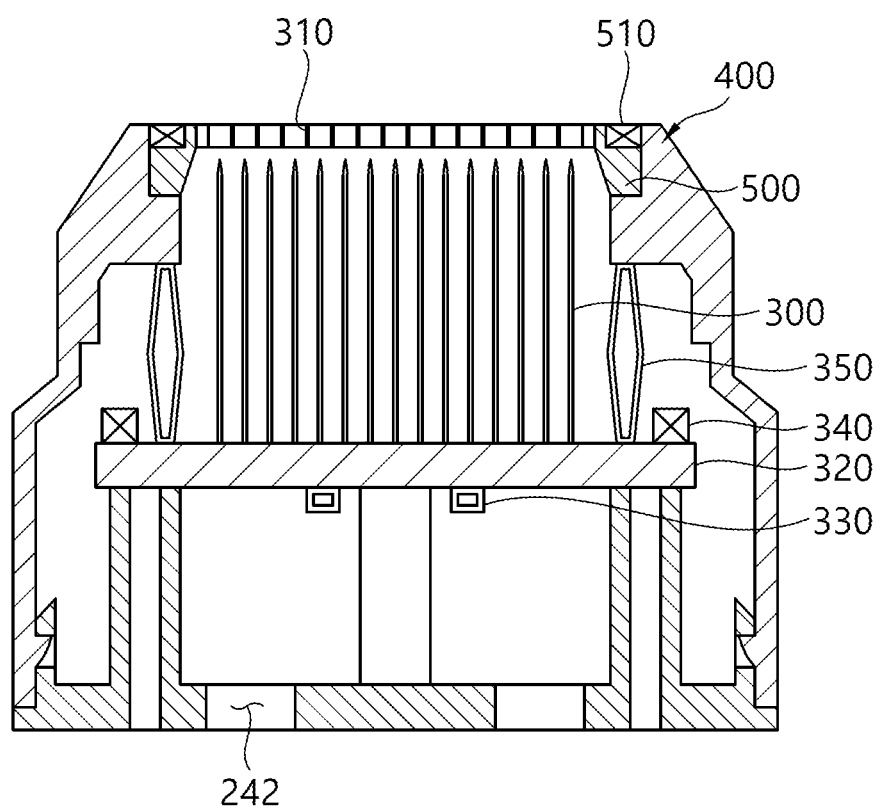
FIG. 3 is a cross-sectional view showing an upper part of the handpiece according to an embodiment of the present invention.

FIG. 3 is a cross-sectional view showing an upper part of the handpiece according to an embodiment of the present invention. Referring to FIG. 3, the end of the handpiece 200 is a portion that comes into contact with a tissue of the human body to perform treatment. A support plate 320 in which the plurality of needles 300 is positioned is provided within the tip module. At least one hole 242 where the output terminal is located is formed at the bottom of the tip module M. The output terminal linearly moves along the hole. A plurality of through holes 310 through which the plurality of needles 300 advances and retracts is formed at the front of the tip module M that forms the end of the handpiece 200. Accordingly, the output terminal 230 is moved by the needle adjustment member 210 to move the support plate, so the plurality of needles 300 is configured to advance and retract through the through holes. In this case, although not shown in the drawing, a separate elastic member 350 pressurizing the support plate 320 toward the output terminal 230 may be configured to be provided on the support plate 320 so that the support plate and the output terminal operate in conjunction with each other. In this case, in addition to the aforementioned structure, the driving structure of the needles may be configured in various manners.

Meanwhile, a current connector 330 may be positioned on the other side of the support plate 320. The current connector 330 is electrically connected to the connection unit 900, so RF energy generated by the RF generator of the main body is delivered. The current connector 330 may be divided into a positive connector to which the positive line of the connection unit is connected and a negative connector to which the negative line of the connection unit is connected. Furthermore, an electrical circuit may be printed on the support plate 320. The electrical circuit is formed so that RF energy delivered to the current connector 330 is delivered to the plurality of needles 300. The electrical circuit may be divided into a positive electrical circuit electrically connected to the positive connector and a negative electrical circuit electrically connected to the negative connector. Accordingly, the plurality of needles 300 may be classified into a plurality of positive needles and a plurality of negative needles. When the positive needles and the negative needles are electrified through the medium of a skin tissue in the state in which they have been inserted into the skin, deep heat is generated in the skin tissue.

Figure 4:
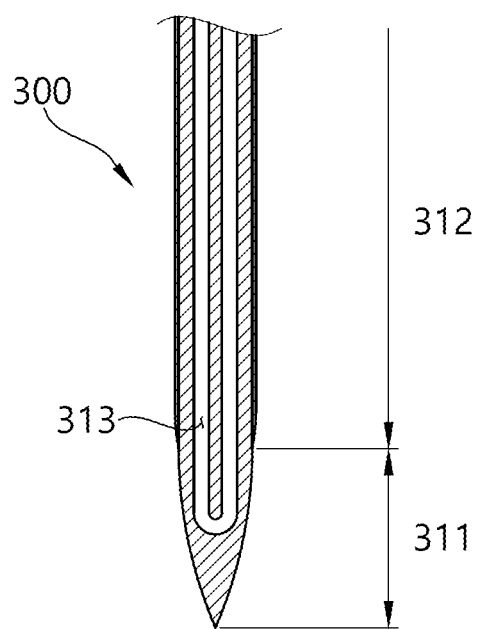
FIG. 4 is a cross-sectional view showing a cross section of the needle in FIG. 3.

FIG. 4 is a cross-sectional view showing a cross section of the needle in FIG. 3. The configuration of the needle of the present embodiment is described in detail with reference to FIG. 4. A plurality of micro needles may be used as the plurality of needles 300. That is, each needle 300 may have a diameter of approximately 5 to 500 μm, and may have a diameter of approximately 15 to 25 μm, for example. In each needle 300, a portion on the front end side is made of a conductive material to form an electrode 311 delivering RF energy. The electrode is formed to have a length of 1 mm or less from the front end of the needle, and may be formed to have a length of 0.1 to 0.5 mm, for example. Furthermore, an insulating part 312 coated with an insulating material, such as silicon, is formed in a section of approximately 200 μm of each needle 300 from the boundary of the electrode. The insulating part 312 prevents RF energy from being delivered to a portion other than a portion for treatment.

Furthermore, a refrigerant circulation path 313 may be formed within each needle 300. The refrigerant circulation path 313 allows a refrigerant, such as a coolant, to circulate within each needle 300, thereby being capable of preventing each needle 300 and a treatment portion from being overheated.

Referring back to FIG. 3, the treatment apparatus according to the present embodiment may include a pressurization unit 400 and a sensing unit 500. The pressurization unit 400 is an element that pressurizes a skin surface toward the direction in which the needles are inserted so that the skin surface into which the needles are inserted has tension of a specific level or more. The pressurization unit 400 is provided. Furthermore, the sensing unit 500 is an element that senses a force that the pressurization unit 400 pressurizes the skin in order to form tension in the skin before the plurality of needles 300 is inserted into the skin.

First, the pressurization unit 400 may be positioned on a contact surface where the skin and the handpiece 200 come into contact with other. Specifically, the pressurization unit 400 may be provided on a surface of the end of the handpiece 200 where the plurality of needles 300 advances and retracts. For example, the pressurization unit 400 has a flat surface and may be configured to pressurize the skin with a force of a specific level or more in the state in which it has come into contact with the skin. An operation of pressurizing, by the pressurization unit, the skin may be performed in such a manner that an operator pressurizes the skin in the state in which the operator has graphed the handpiece, or the pressurization unit may be configured to pressurize the skin by a separate driving unit.

The force that pressurizes the skin using the pressurization unit 400 may be differently applied depending on the skin state of a patient, and the force of at least 1N may be applied in order to generate tension of a specific amount or more.

The pressurization unit 400 may first come into contact with the skin before the plurality of needles 300 is inserted into the skin, and may pressurize the skin. If the plurality of needles is inserted into the skin in the state in which there is almost no surface tension of the skin, it is difficult for the needles to penetrate the skin surface, thereby causing a lot of pain for a patient. Accordingly, the pressurization unit 400 may raise skin tension by pressurizing the skin before the needles 300 are inserted into the skin, and in this state, the needles 300 are inserted into the skin, thereby being capable of improving convenience of a surgical procedure and reducing a patient's pain.

The pressurization unit 400 may be integrally provided at the end of the handpiece 200 or the tip module M through calking joint. Furthermore, since an elastic skin is inclined or forms a curve, the pressurization unit 400 may include an elastic member having an elastic force and capable of forming a slope along a bent skin surface in order to maximize the area where the pressurization unit 400 comes into contact with the skin surface. For example, the pressurization unit 400 may be made of a silicon rubber block, glass or plastic that does not damage the skin.

Figure 5:
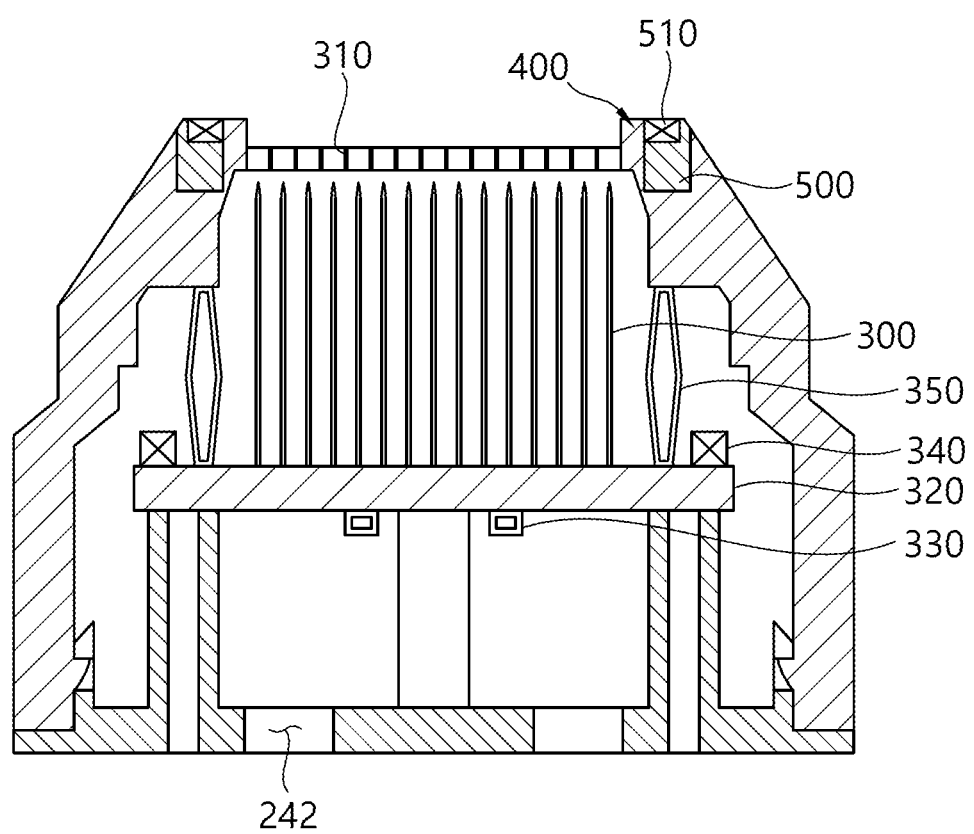
FIG. 5 is a cross-sectional view of an upper part of the handpiece according to another embodiment of the present invention.

In FIG. 3, the pressurization unit has been illustrated as being coplanar with a cross section of the handpiece in which the through holes have been formed, but the pressurization unit may be configured to have various structures. For example, FIG. 5 shows the end of the handpiece having the pressurization unit of a different structure. The pressurization unit 400 of the handpiece shown in FIG. 5 may be disposed in the periphery of the through holes 310 through which the plurality of needles 300 penetrate, and may be provided to have a stepped structure with respect to the surface where the through holes are disposed. That is, the pressurization unit 400 may be positioned in a circular ring form at the end of the handpiece 200, and may be configured to have a form protruded from the surface where the through holes have been formed. In this case, the pressurization unit may be configured to have the same height so that one plane comes into contact with the skin. Alternatively, the pressurization unit itself may have a structure having a step, a prominence and depression, and a protrusion, so the pressurization unit comes into contact with the skin at a plurality of locations to pressurize the skin. In addition, the structure of the pressurization unit may be changed in various manners.

Meanwhile, as described above, the sensing unit 500 may sense a force applied to the skin by the pressurization unit 400 so that tension of a given amount or more is generated in the skin. The sensing unit 500 may be positioned at a location neighboring the top or bottom of the pressurization unit 400 and may be configured using various sensors.

For example, as shown in FIG. 3, the sensing unit 500 according to the present embodiment may be configured to include a pressure sensor 510. The pressure sensor 510 is formed at a location neighboring the pressurization unit 400. For example, the pressure sensor may be positioned on a surface that belongs to the pressurization unit and comes into contact with the skin or may be positioned on one side (an inward direction in which the through holes are formed) of the pressurization unit. Alternatively, the pressurization unit may be made of a transparent material and the pressure sensor may be formed within the pressurization unit depending on a measuring method of the pressure sensor.

The sensor of the present embodiment is named the pressure sensor, and includes a variety of sensors capable of measuring tension of the skin or sensing information, such as pressure applied to the skin. Furthermore, various sensors, such as a displacement conversion type, a physical conversion type, a force equilibrium type, a vibration type and a gyro type, may be used as the pressure sensor 510.

Information sensed by the sensing unit 500 may be used to determine whether tension of the skin corresponding to a treatment location has been sufficiently formed by the pressurization unit 400. For example, when a force or pressure applied by the pressurization unit 400 exceeds a set reference value, it may be determined that sufficient tension has been applied to the skin of a corresponding location. In this case, although the pressurization unit 400 applies the same force to the skin, tension formed in each skin may be different depending on the sex, human race, age, treatment location, etc. of a patient. Accordingly, a reference value at which the sensing unit 500 determines that sufficient tension has been applied to the skin may be controlled by a user.

In the present embodiment, the sensing unit 500 determines whether sufficient tension is formed in the skin based on the amount of force applied to the skin by the pressurization unit 400, but the present invention is not limited thereto. In a modified implementation, the sensing unit may determine whether sufficient tension is formed in the skin based on different information (e.g., information on an image of a skin surface).

Figure 6:
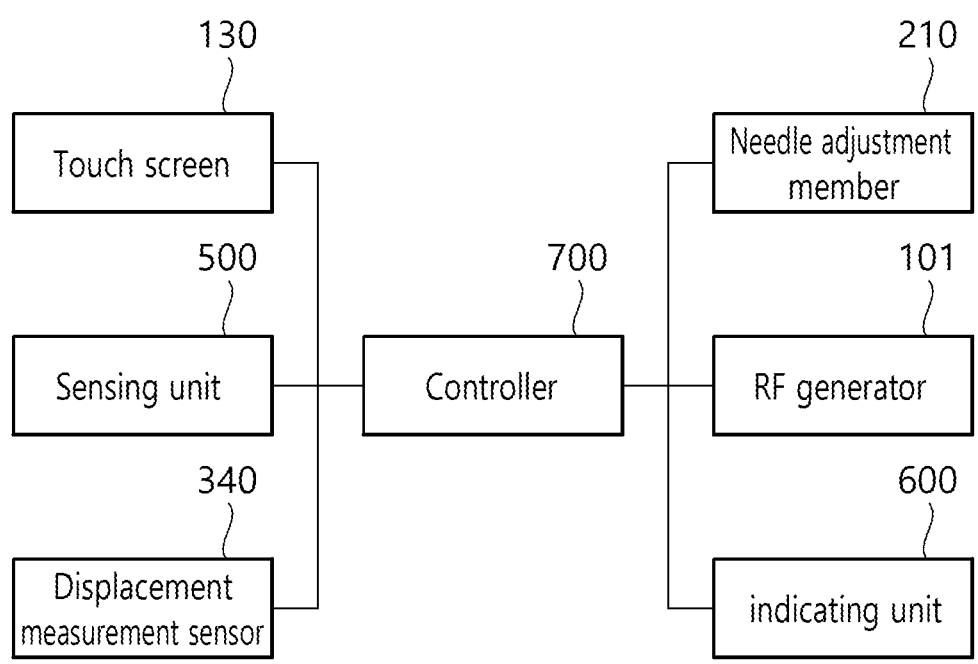
FIG. 6 is a block diagram showing control contents of a controller in the treatment apparatus of FIG. 2.

FIG. 6 is a block diagram showing control contents of a controller in the treatment apparatus of FIG. 2. As shown in FIG. 6, the controller 700 may receive a variety of types of information from the touch screen 130, the sensing unit 500 or the displacement sensing unit 340. Furthermore, the controller may control the operation of the needle adjustment member 210, the RF generator 101 or the indicating unit 600 based on the information.

Specifically, a user may input various treatment parameters, such as the output, pulse form, treatment time, etc. of the treatment apparatus through the touch screen 130. Furthermore, the controller 700 may drive various elements, such as the needle adjustment member and the RF generator, based on information received through the touch screen 130 or an operating mode stored in the memory of the controller.

Furthermore, as described above, the sensing unit 500 may determine whether sufficient tension has been applied to a treatment location prior to a surgical procedure. The controller 700 may perform control based on information sensed by the sensing unit 500. For example, if the sensing unit 500 determines that skin tension at a corresponding location has been sufficiently formed, the controller 700 may notify a user that skin tension has been sufficiently formed by indicating it on the indicating unit 600 (refer to FIG. 2) of the handpiece. Alternatively, the controller 700 may control the needle adjustment member 210 and the RF generator 101 so that they operate only in the state in which skin tension at a corresponding location satisfies reference conditions in the sensing unit 500. Accordingly, the plurality of needles is inserted into the skin at the same time or sequentially. RF energy may be delivered to a skin tissue in the state in which the plurality of needles has been inserted into the skin.

Moreover, the treatment apparatus according to the present invention may further include a displacement measurement sensor 340. As shown in FIG. 3, the displacement measurement sensor 340 is an element positioned at the end of the handpiece to measure displacement in which the needles 300 are moved. Accordingly, the depth of the needle 300 inserted into a tissue during treatment may be determined based on information sensed by the displacement measurement sensor 340. In FIG. 3, the displacement measurement sensor 340 is positioned on the support plate, but a measurement method and measuring location may be changed by a user in various manners.

In inserting the needles 300 into the human body and performing treatment, the controller 700 may control the operation of the needle adjustment member 210 while feeding back whether the electrodes of the needles have reached a target depth based on a value sensed by the displacement measurement sensor 340. Alternatively, in order to prevent the needles from being deep inserted into the human body due to the malfunction of the needle adjustment member 210, when the insertion of the needles 300 into a given depth or more is sensed by the displacement measurement sensor 340, the controller 700 may control the operations of the needle adjustment member 210 and/or the RF generator 101 so that they are automatically stopped.

FIG. 6 shows that the controller receives information necessary for control from the touch screen, the sensing unit, and the displacement measurement sensor and controls the operations of the needle adjustment member, the RF generator, and the indicating unit based on the information. This is only an example. The controller may receive information necessary for control from an element other than the elements shown in FIG. 6, and may control the operation of the element other than the elements shown in FIG. 6.

For example, although not separately shown, an interval measurement sensor for measuring the interval between the pressurization unit and a skin surface when the needles are inserted may be further included. In the state in which the pressurization unit has pressurized a skin surface before a needle insertion operation is performed, the pressurization unit and the skin surface form the same plane (the state in which the skin surface has come into contact with a surface of the end of the handpiece in the case of FIG. 3 and the state in which the skin surface is coplanar with the plane of the end of the pressurization unit in the case of FIG. 5). In contrast, when the needles perform an insertion operation, a phenomenon in which the skin surface is pressed toward the direction in which the needles are pressed occurs as the needles pressurize the skin surface. Accordingly, although the depth that the needles are inserted is determined using the displacement measurement sensor when the needle insertion operation is performed, the needles may not be inserted into a desired depth because the location of the skin surface is changed. Accordingly, the interval measurement sensor may measure the interval between the pressurization unit (or the end of the handpiece) and a skin surface formed by the pressurization of the needles when the needles are inserted, and may control the insertion depth of the needles based on the measured interval. Accordingly, the controller 700 may control to adjust the advancing displacement of the needles by taking into consideration a value measured by the interval measurement sensor so that a depth that the needles have not been inserted is compensated for while the skin is pressurized.

Hereinafter, an operation of the treatment apparatus according to the present invention is described in detail with reference to the accompanying drawings.

Figure 7:
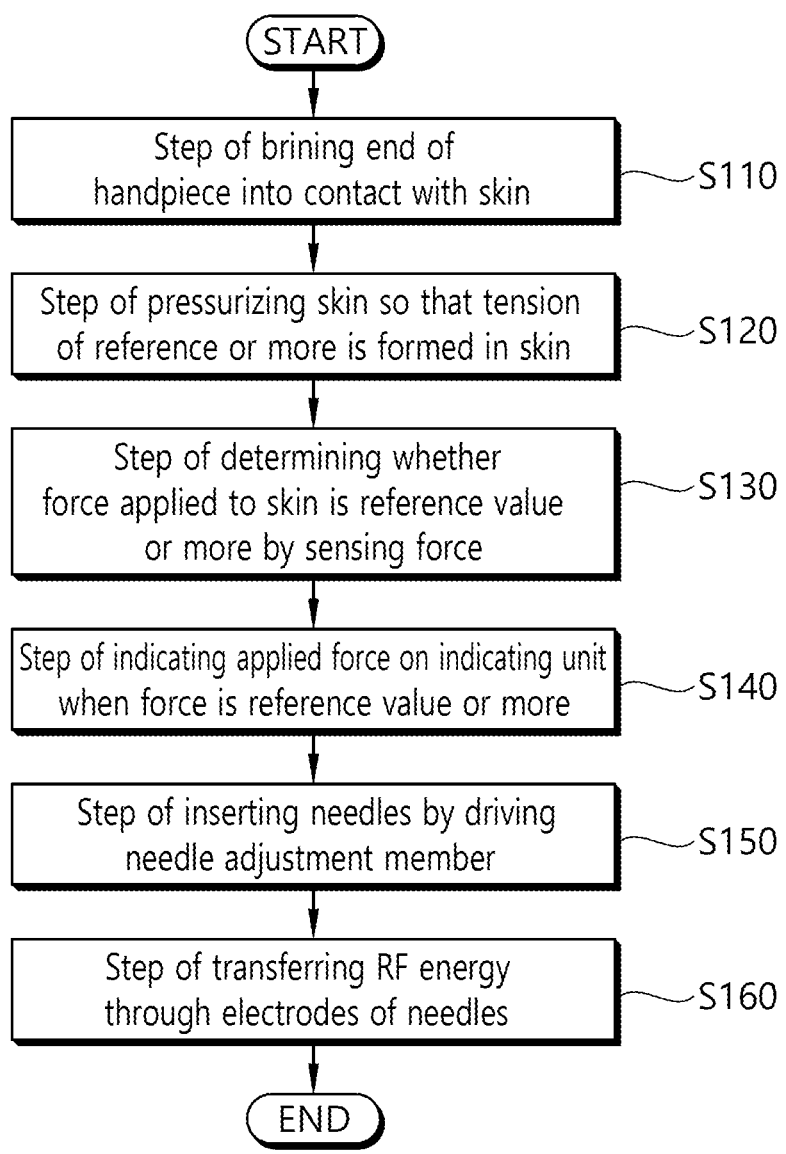
FIG. 7 is a flowchart showing a first operation method using the treatment apparatus according to the present invention.
Figure 8:
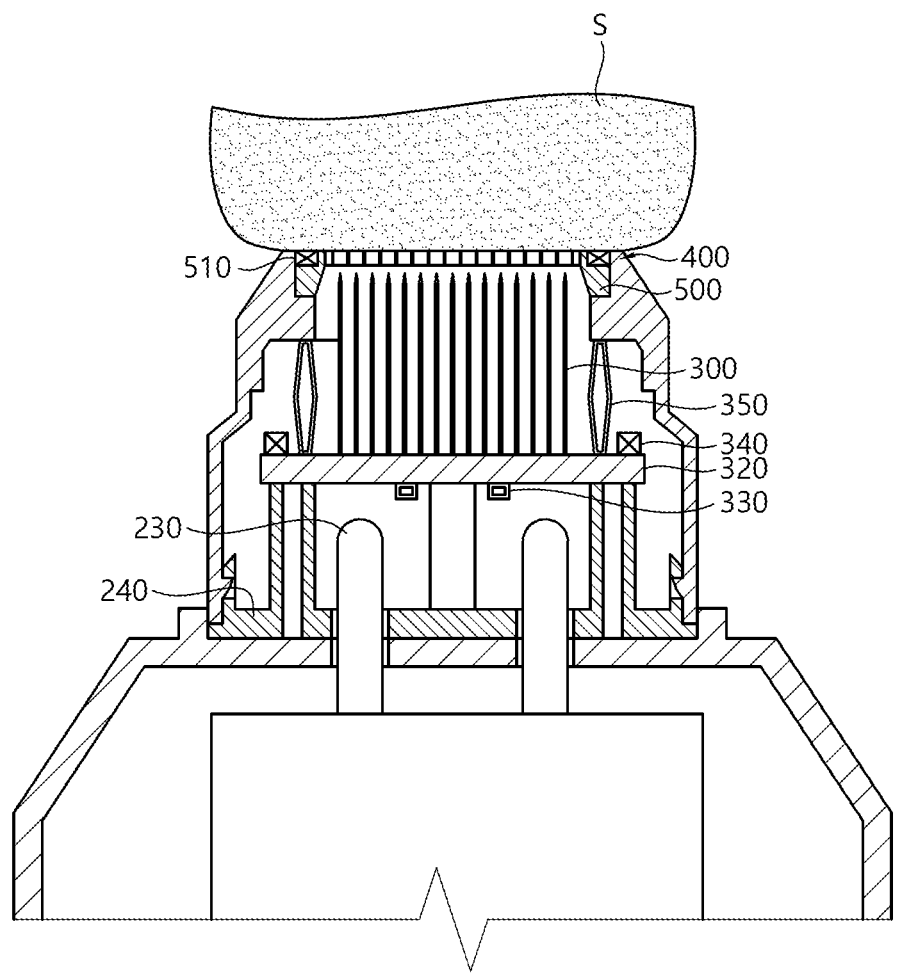
FIG. 8 is a cross-sectional view showing a step of coming, by the handpiece, into contact with the skin in FIG. 7.
Figure 9:
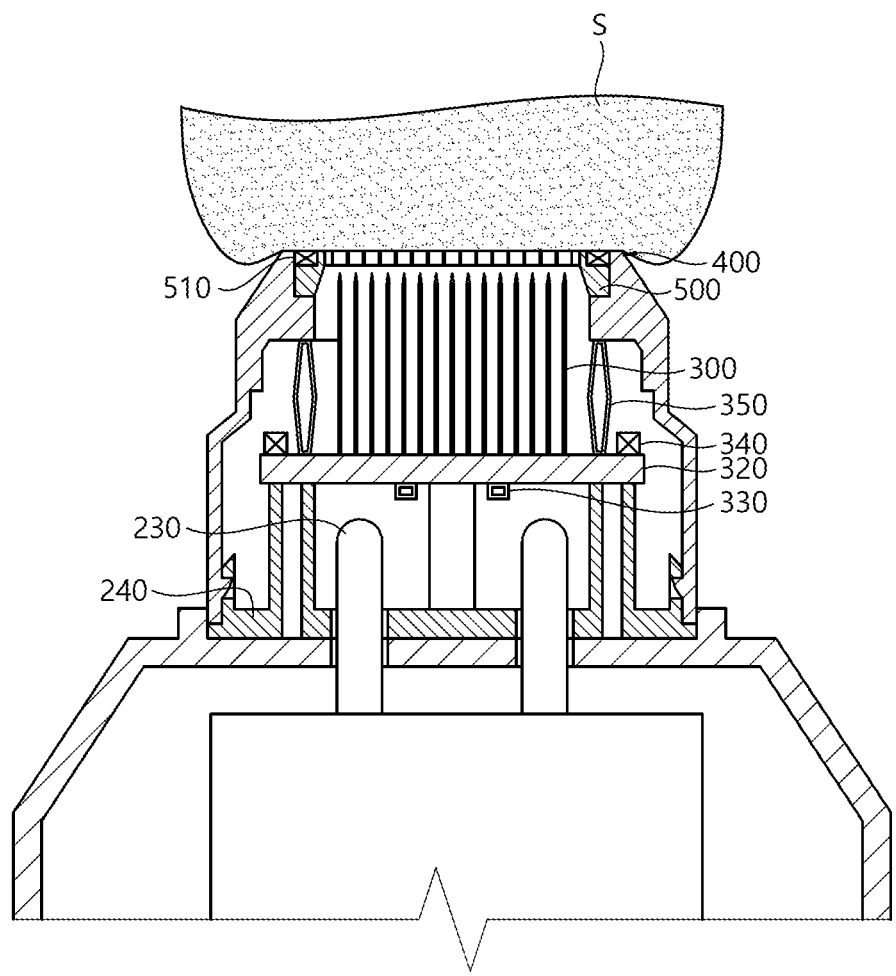
FIG. 9 is a cross-sectional view showing a step of applying, by the handpiece, pressure in FIG. 7.
Figure 10:
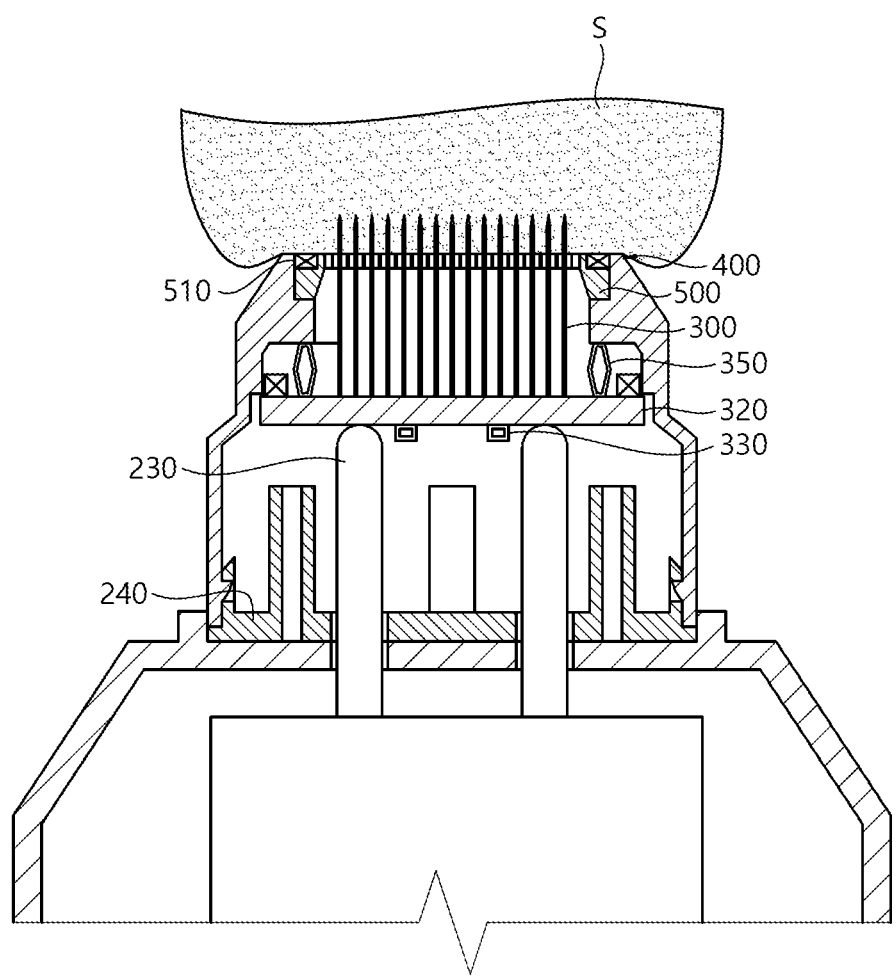
FIG. 10 is a cross-sectional view showing a step of inserting needles in FIG. 7.

FIG. 7 is a flowchart showing a first operation method using the treatment apparatus according to the present invention. FIGS. 8 to 10 are cross-sectional views showing operations of the treatment apparatus in major steps of FIG. 7.

First, the step of positioning the handpiece 200 at a treatment location that requires treatment and bringing the end of the handpiece into contact with the skin is performed (S110) (refer to FIG. 8). As shown in FIG. 8, in this step, the needles 300 of the handpiece remain not protruded to the outside.

In the state in which the end of the handpiece has come into contact with the skin, the step of pressurizing the skin using the pressurization unit 400 is performed (S120) (refer to FIG. 9). In this step, a user may directly pressurize the skin in the state in which he or she has grasped the handpiece. If the pressurization unit has a structure capable of performing a pressurization operation through a separate pressurization mechanism, the skin may be pressurized using the pressurization mechanism. As shown in FIG. 9, when this step is performed, tension on a surface of the skin at a corresponding location is increased as the skin is pressurized by the pressurization unit 400.

Meanwhile, while the skin is pressurized by the pressurization unit 400, the sensing unit 500 measures a force that the pressurization unit 400 pressurizes the skin. Such measurement may be performed consecutively or in a given cycle while the step S120 is performed. In order to determine whether proper tension has been formed in the skin, the step of comparing the measured value with a reference value is performed (S130).

If it is determined that tension of a reference or more has been formed in the skin based on information measured by the sensing unit 500 (when the measured value is the reference value or more), the controller 700 performs the step of indicating it on the indicating unit 600 (S140). The indicating unit may be configured using various devices capable of indicating information for a user through a sense of sight or a sense of hearing, such as a liquid crystal display, a light-emitting element and a bell. The user may confirm that skin tension at the treatment location is the reference value or more through the indicating unit 600.

Thereafter, the user may drive the needle adjustment member 210 through a manipulation (S150) (FIG. 10). Specifically, when the user manipulates a driving switch (not shown) included in the handpiece, the controller 700 drives the needle adjustment member 210. At this time, as shown in FIG. 10, the output unit 230 moves toward the end of the handpiece through the hole 242 formed in the base 240 of the tip module, thus moves the support plate 320. Accordingly, the plurality of needles 300 is inserted into a tissue through the skin surface in which tension has been formed. At this time, an insertion depth can be adjusted through the displacement measurement sensor 340 while the depth of the inserted needles is fed back, or when the insertion of the needles into a set depth or more is sensed, the controller may control to stop the operation of the needle adjustment member.

In this case, if the treatment apparatus including the interval measurement sensor is used, the controller may control to adjust the insertion depth of the needles by additionally advancing the needles by taking into consideration the displacement of a skin surface that is measured by the interval measurement sensor and that occurs due to the pressurization of the needles when the needles are inserted.

When the needles 300 reach a target depth inside the tissue through the step, the step of transferring RF energy generated by the RF generator to the tissue through the electrodes 311 at the ends of the needles is performed (S160). When the RF energy is transferred, deep heat is generated within the skin tissue and thus treatment is performed.

Figure 11:
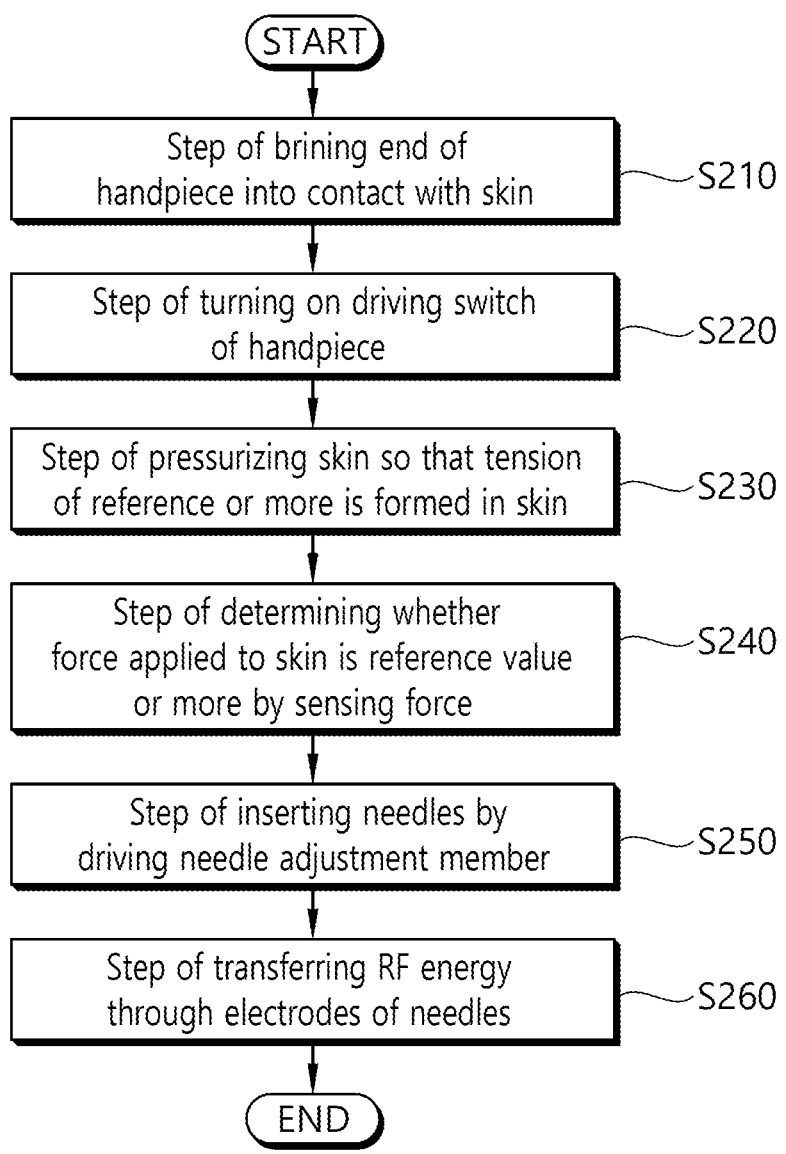
FIG. 11 is a flowchart showing a second operation method using the treatment apparatus according to the present invention.

FIG. 11 is a flowchart showing a second operation method using the treatment apparatus according to the present invention. The first operation method is a method for a user to confirm that tension of a reference or more has been formed in the skin through the indicating unit, to insert the needles and to perform treatment. In contrast, the second operation method may be performed in such a manner that when the formation of skin tension of a reference or more is sensed while a user pressurizes the skin using the handpiece, the needle adjustment member automatically operates to insert the needles and thus treatment is performed. The second operation method is described in detail below with reference to FIG. 11. In this case, a detailed description of a step similar to the step of the first operation method is omitted.

Specifically, as shown in FIG. 11, the step of positioning the handpiece at a treatment location that requires treatment and bringing the end of the handpiece into contact with the skin is performed (S210).

When the location of the handpiece is determined through the step, a user manipulates the driving switch in the on state (S220). This state may be a preliminary mode in which the needles 300 are inserted. This may be the state in which an operation of inserting the needles 300 automatically is performed when a specific condition (in this case, a condition in which skin tension of a reference or more is formed) is satisfied.

In the aforementioned on state, the step of pressurizing the skin using the pressurization unit 400 is performed (S230). Furthermore, while the skin is pressurized by the pressurization unit 400, the sensing unit 500 measures a force that the pressurization unit 400 pressurizes the skin and simultaneously compares a measured value with a reference value (S240).

Through the step, it is determined that skin tension has not been sufficiently formed if the force pressurized by the pressurization unit 400 does not reach the reference value, and a needle insertion operation is not performed. Furthermore, if another condition is satisfied, for example, when a specific time (0.1 to 2 seconds) elapses or when the release of a contact state is sensed by a sensor (not shown) that senses whether the handpiece has come into contact with the skin, a configuration may be performed so the on state switches to an off state.

In contrast, if the force pressurized by the pressurization unit 400 is the reference value or more, the controller 700 determines that skin tension has been sufficiently formed. The controller 700 performs the step of inserting the needles by driving the needle adjustment member 210 (S250). Furthermore, when the needles 300 are inserted and reach a target depth, treatment is performed by transferring RF energy through the electrodes of the needles (S260).

Figure 12:
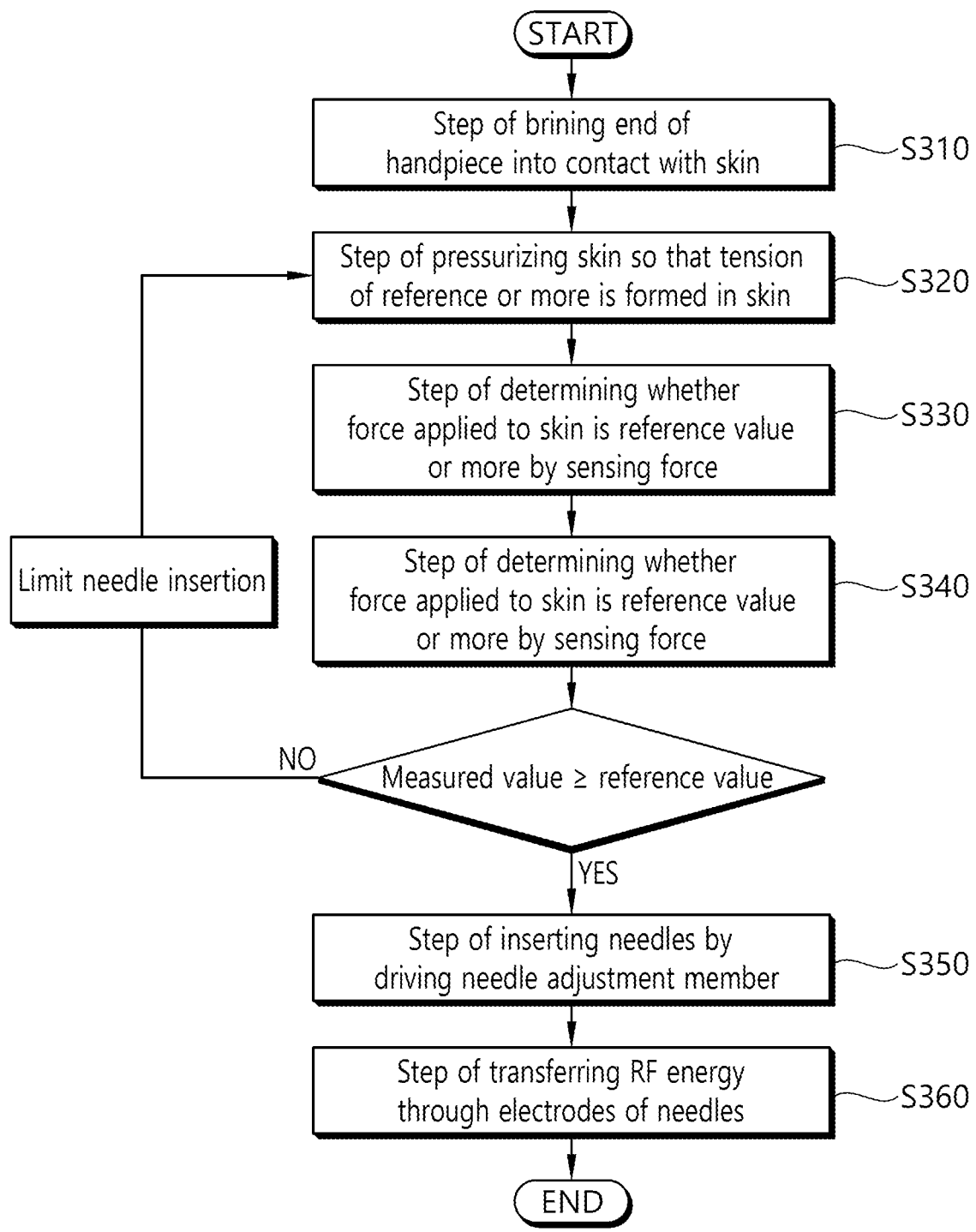
FIG. 12 is a flowchart showing a third operation method using the treatment apparatus according to the present invention.

FIG. 12 is a flowchart showing a third operation method using the treatment apparatus according to the present invention. The second operation method is a method of automatically inserting the needles when skin tension of a reference value or more is formed. In contrast, the third operation method is a method of limiting a needle operation in despite of a user's manipulation if skin tension is not sufficiently formed when the user performs treatment. The third operation method is described in detail with reference to FIG. 12. In this case, a detailed description of a step similar to the step of the first and second operation methods is omitted.

Specifically, as shown in FIG. 12, the step of positioning the handpiece at a treatment location that requires treatment and brining the end of the handpiece into contact with the skin is performed (S310).

When the location of the handpiece is determined through the step, the step of pressurizing the skin using the pressurization unit 400 is performed (S320). Furthermore, while the skin is pressurized by the pressurization unit 400, the sensing unit 500 measures a force that the pressurization unit 400 pressurizes the skin and simultaneously compares a measured value with a reference value (S330).

Furthermore, a user may perform a needle insertion operation by manipulating the handpiece in the state in which the skin has been pressurized (S340). For example, the user may manipulate the driving switch included in the handpiece. Accordingly, a command signal to drive the needle adjustment member may be transferred to the controller (in this case, the driving switch is an element that generates a signal to immediately perform the needle insertion operation unlike in the second operation method).

In this case, when the user manipulates the driving switch, if a value measured by the sensing unit 500 is the reference value or more, the controller 700 may control to perform an operation of inserting the needles as the user has intended (S350). In contrast, if a value measured by the sensing unit 500 is less than the reference value, the controller 700 may determine that skin tension has not been sufficiently formed and limit the operation of inserting the needles in despite of an operation command from the user. Likewise, the user is induced to perform the needle insertion operation while pressurizing the skin with a gradually greater force while repeating the above step. Accordingly, it can prevent pain on a patient from being aggravated as the needles are inserted in the state in which sufficient tension has not been formed in the skin.

When the needles 300 are inserted into the target depth inside the skin through the step, treatment is performed by transferring RF energy through the electrodes 311 of the needles (S360).

Although the first to third operation methods of the treatment apparatus according to the present invention have been described, various operation methods may be implemented using information related to tension of the skin sensed by the sensing unit.

Furthermore, although the embodiments of the present invention have been described with reference to the accompanying drawings, a person having ordinary skill in the art to which the present invention pertains will understand that the present invention may be practiced in other detailed forms without changing the technical spirit or essential characteristics of the present invention. Therefore, it should be understood that the aforementioned embodiments are illustrative from all aspects and are not limitative. The scope of the present invention is defined by the appended claims rather than the detailed description, and the meaning and scope of the appended claims and all changes or modified forms derived from equivalents thereof should be construed as being included in the scope of the present invention.

The invention claimed is:

1. An RF energy treatment apparatus, comprising:
a handpiece;
a plurality of needles formed to advance and retract on one side of the handpiece and supplied with a high frequency current;
a pressurization unit positioned in a direction in which the plurality of needles advances and retracts and providing tension to a skin by applying a positive pressure to the skin;
a sensing unit comprising at least one sensor configured to sense an amount of force applied to the skin by the pressurization unit, the amount of force corresponding to the tension that is provided to the skin; and
a controller coupled to the sensing unit,
wherein the sensing unit is configured to compare the amount of force sensed by the sensing unit to a set reference value so that the tension provided to the skin is above a threshold value before the plurality of needles is advanced through the skin,
wherein the pressurization unit includes an elastic member which is configured to deform over curved surfaces of the skin, and wherein an entire tissue-contacting surface of the pressurization unit is planar.

2. The RF energy treatment apparatus of claim 1, further comprising an indicating unit that indicates when the tension provided to the skin is equal to or more than the threshold value.

3. The RF energy treatment apparatus of claim 1, wherein the sensing unit transmits a signal to the controller so that the plurality of needles is inserted into the skin simultaneously or sequentially when the tension provided to the skin is above the threshold value.

4. The RF energy treatment apparatus of claim 1, wherein the pressurization unit is positioned on a surface of an end of the handpiece on the one side where the plurality of needles advances and retracts.

5. The RF energy treatment apparatus of claim 1, wherein:
the pressurization unit is positioned at an edge of a surface through which the plurality of needles penetrates, and
the surface through which the plurality of needles penetrates is recessed below a skin-facing surface of the pressurization unit.

6. The RF energy treatment apparatus of claim 1, wherein the at least one sensor of the sensing unit comprises at least one pressure sensor positioned on a surface of an edge forming the pressurization unit.

7. The RF energy treatment apparatus of claim 1, wherein the force applied by the pressurization unit is 1N or more so that the tension provided to the skin is equal to or more than the threshold value.

8. The RF energy treatment apparatus of claim 1, further comprising a current connector positioned within the handpiece to supply current to the sensing unit and supply the high frequency current to the plurality of needles.

9. The RF energy treatment apparatus of claim 1, further comprising:
a support plate supporting the plurality of needles, and
a displacement measurement sensor positioned at a location neighboring the support plate to measure a depth of the needles inserted into the skin.

10. The RF energy treatment apparatus of claim 1, wherein the set reference value is adjustable based on at least one of a sex, a race, an age or a treatment location of a patient.

* * * * *